(12) United States Patent
Weiner

(10) Patent No.: US 11,234,589 B2
(45) Date of Patent: Feb. 1, 2022

(54) FIELD OF VISION QUANTIFICATION

(71) Applicant: Worcester Polytechnic Institute, Worcester, MA (US)

(72) Inventor: Yonatan Weiner, Tucson, AZ (US)

(73) Assignee: Worcester Polytechnic Institute, Worcester, MA (US)

( * ) Notice: Subject to any disclaimer, the term of this patent is extended or adjusted under 35 U.S.C. 154(b) by 232 days.

(21) Appl. No.: 16/709,088

(22) Filed: Dec. 10, 2019

(65) Prior Publication Data

US 2020/0178790 A1 Jun. 11, 2020

Related U.S. Application Data

(60) Provisional application No. 62/777,465, filed on Dec. 10, 2018.

(51) Int. Cl.
*A61B 3/024* (2006.01)
*A61B 3/00* (2006.01)

(52) U.S. Cl.
CPC ............ *A61B 3/024* (2013.01); *A61B 3/0083* (2013.01); *A61B 3/0091* (2013.01)

(58) Field of Classification Search
CPC ...... A61B 3/024; A61B 3/0091; A61B 3/0083
USPC ........................................................ 351/224
See application file for complete search history.

(56) References Cited

U.S. PATENT DOCUMENTS

| | | |
|---|---|---|
| 4,429,961 A | 2/1984 | Sheingorn |
| 5,220,361 A | 6/1993 | Lehmer et al. |
| 7,926,943 B1 * | 4/2011 | Reichow ................ A61B 3/024 351/203 |
| 2006/0058619 A1 * | 3/2006 | DeYoe .................... G06T 11/00 600/407 |
| 2011/0299034 A1 * | 12/2011 | Walsh .................. A61B 5/0073 351/206 |
| 2013/0339043 A1 * | 12/2013 | Bakar .................. A61B 5/0205 705/2 |

FOREIGN PATENT DOCUMENTS

DE 102015222844 A1 5/2017

OTHER PUBLICATIONS

International Search Report, PCT/US2019/065411/, dated Feb. 25, 2020, pp. 1-2.

* cited by examiner

*Primary Examiner* — Mohammed A Hasan
(74) *Attorney, Agent, or Firm* — Armis IP Law, LLC

(57) ABSTRACT

A field of vision assessment is performed by reported positional feedback of visual markers at an outer circumference of a subject's field of vision. An array of visual markers arranged in a grid is rendered near a peripheral vision limit of the subject. The visual markers are disposed at known locations relative to an origin of the field of vision of the subject. Based on reported visual markers, a mapping of the visual markers to the location denotes a point on a periphery of limit of the visual field. The mapped points define vertices of a polyhedron having edges denoted by the vertices and the origin. The volume of the resulting polyhedron correlates to the field of vision of the subject, since as the periphery of the field of vision increases, the computed volume also increases.

15 Claims, 4 Drawing Sheets

FIELD OF VISION QUANTIFICATION

RELATED APPLICATIONS

This patent application claims the benefit under 35 U.S.C. § 119(e) of U.S. Provisional Patent App. No. 62/777,465, filed Dec. 10, 2018, entitled "FIELD OF VISION QUANTIFICATION," incorporated herein by reference in entirety.

BACKGROUND

Field of vision assessment and measurement are routinely performed by optometrists and vision professionals, and involve the use of expensive and invasive test apparatus that examine an anatomy of human vision organs (eyes and related structures). The measured field of vision is typically expressed as an angular value denoting an ability to perceive visual images within an offset equal to or less than the angular value. The angular value is typically taken for left, right, up and down directions from a front facing orientation of a human test subject, and typically perform some kind of retinal positional assessment based on a direct evaluation of the eye structure.

SUMMARY

A field of vision assessment is performed by reported positional feedback of visual markers at an outer circumference of a subject's field of vision. An array of visual markers arranged in a grid is rendered near a peripheral vision limit of the subject. The visual markers are disposed at known locations relative to an origin of the field of vision of the subject. Based on reported visual markers, a mapping of the visual markers to the location denotes a point on a periphery of limit of the visual field. The mapped points define vertices of a polyhedron having edges denoted by the vertices and the origin. The volume of the resulting polyhedron correlates to the field of vision of the subject, since as the periphery of the field of vision increases, the computed volume also increases. The volume may be employed as a baseline for successive iterations, such that a decrease in peripheral vision results in a decreasing computed volume. In contrast to complicated and invasive retinal examination, the volume of a polygon defined by an outer perimeter of the peripheral vision is an effective indicator of a stable or decreasing field of vision.

The disclosed approach demonstrates that by capturing vertices defining a bounded polyhedron and determining a FOV based on a computed volume of the bounded polyhedron, a baseline change may be determined for indicating if more invasive approaches are warranted. The disclosed approach may be employed as a low cost, non-invasive screening adaptable for on-site setup in a variety of locations such as doctor's offices, eyeglass vendors, urgent care and non-hospital examination locations, and sports event and training facilities for detection of adverse head impacts and injuries.

Configurations herein are based, in part, on the observation that peripheral vision is often employed as an indicator of overall ocular health. Unfortunately, conventional Field of View (FOV) evaluations require expensive electronics and computing facilities for invasive examination of the eye and retina structure. Accordingly, configurations herein substantially overcome the shortcomings of conventional approaches by rendering a low-cost visual marker array for identifying and capturing vertices defining a bounded polyhedron and determining a FOV based on a computed volume of the bounded polyhedron.

Configurations herein demonstrate a vision field assessment device, including an array of visual markers approximating an outer range of a field of view, such that each visual marker has a position in the array. The array is referenced by a mapping from a field of view (FOV) origin to each visual marker in the array, typically by a reported stream of input depicting which markers are visible in a subject's peripheral vision. The mapping has a plurality of elements corresponding to the visual markers, and each element in the plurality of elements stores a position from the FOV origin to the corresponding visual marker. Each position of a visible marker defines a vertex of a polyhedron and an edge from the origin, such that a volume of the polyhedron quantifies the field of view.

In a particular approach, the marker grid is employed for quantifying a field of vision by receiving a set of indications of a visual marker, such that each visual marker has a position in an array of visual markers. A mapping of each of the indications to a position defines a location relative to an origin of a field of vision. The positions are employed to form a polyhedron having edges defined by each of the positions and the origin of the field of vision. A volume is computed of the defined polyhedron to generate a quantifiable measure of the field of vision.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Depicted below is an example configuration of the vision field assessment device in several configurations. Each of the configurations is compatible with the others and demonstrate a progression from a minimal configuration to the most encompassing configuration. The disclosed visual marker array may be disposed on any orientation in the subject's field of view, and may be of a linear or two dimensional arrangement. Generally, a particular configuration may include opposed right and left visual marker arrays, due to the logistic issues of positioning visual markers above and below the subject's field of vision. The visual markers may be a painted, inked or lighted arrangement of symbols in a grid form, as will be described further below. They may also be rendered on an LED, LCD or similar electronic display, or depicted by lighted signals, if sufficient power is available.

Figure 1:
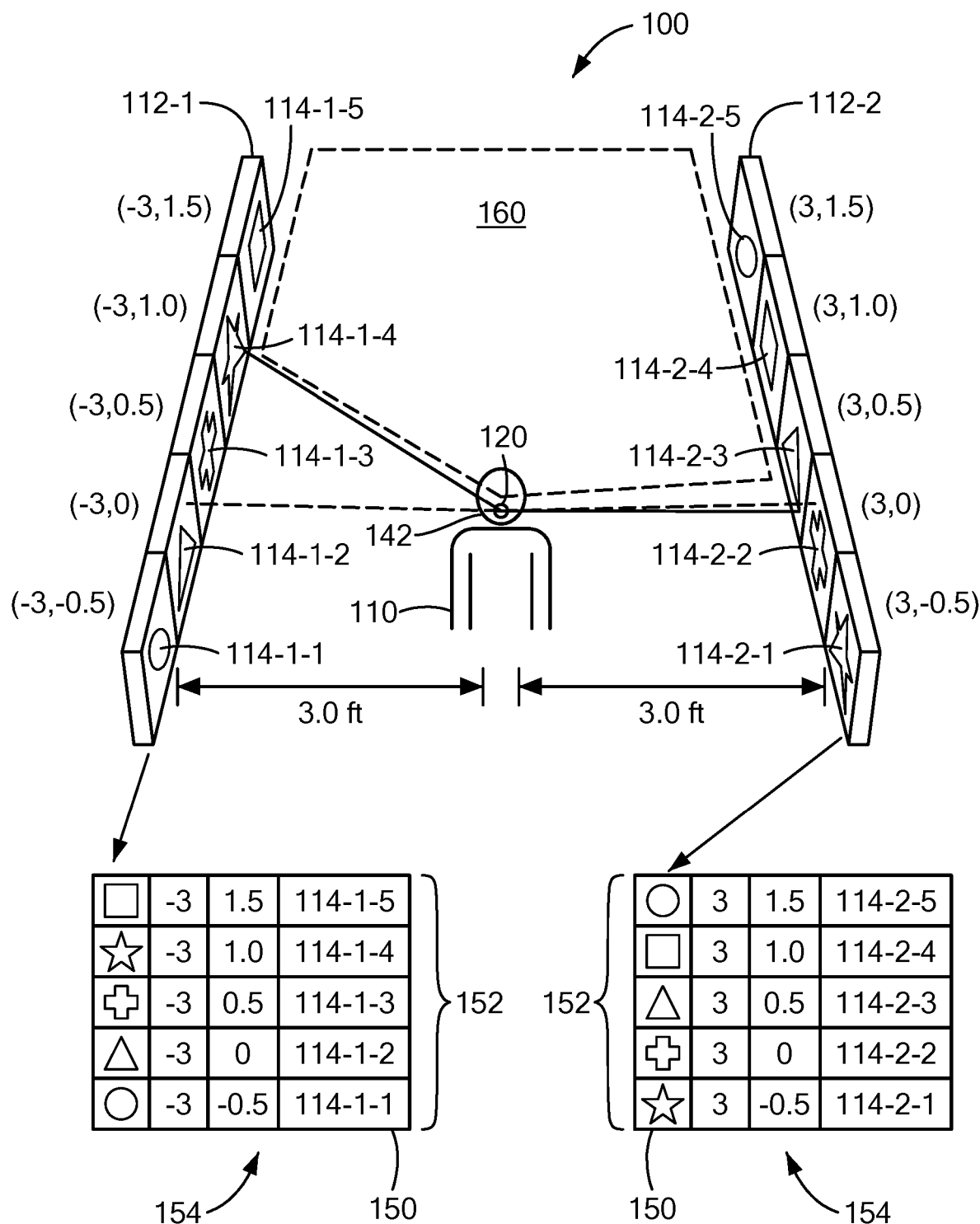
FIG. 1 is a perspective view of a configuration employing the vision assessment device as disclosed herein.

FIG. 1 is a perspective view of a vision field assessment device as disclosed herein. Referring to FIG. 1, in a vision assessment environment 100, a test subject (subject) 110 sits or stands between left and right visual marker displays 112-1, 112-2 respectively (112 generally). Each of the marker displays 112 includes a plurality of symbols 114-1-1 . . . 114-2-5 (114 generally), having a position from the origin 120 defined by a chinrest 142. FIG. 1 shows a single dimensioned marker display, however two dimensions may be employed as in FIG. 2, below.

A mapping 150 stores an element 152-N corresponding to each symbol 114 and including the corresponding position 154. The array 112 of visual markers approximates an outer range of a field of view of the subject 110, such that each visual marker 114 maps to an element 152 of a position 154 in the array 112. The array 112 is referenced by the mapping from the field of view (FOV) origin 120 for each visual marker 114 in the array 112. The mapping 150 therefore includes a plurality of elements 152 corresponding to the visual markers 114. Each element 152 stores a respective position 154 from the FOV origin 120 to the corresponding visual marker 114. Each position 154 defines a vertex of a polyhedron and an edge from the origin such that a volume of the polyhedron quantifies the field of view, discussed further below in FIG. 3. A resulting area 160 may be employed to generate a 3 dimensional representation of a FOV by extending the area into a polyhedron.

Figure 2:
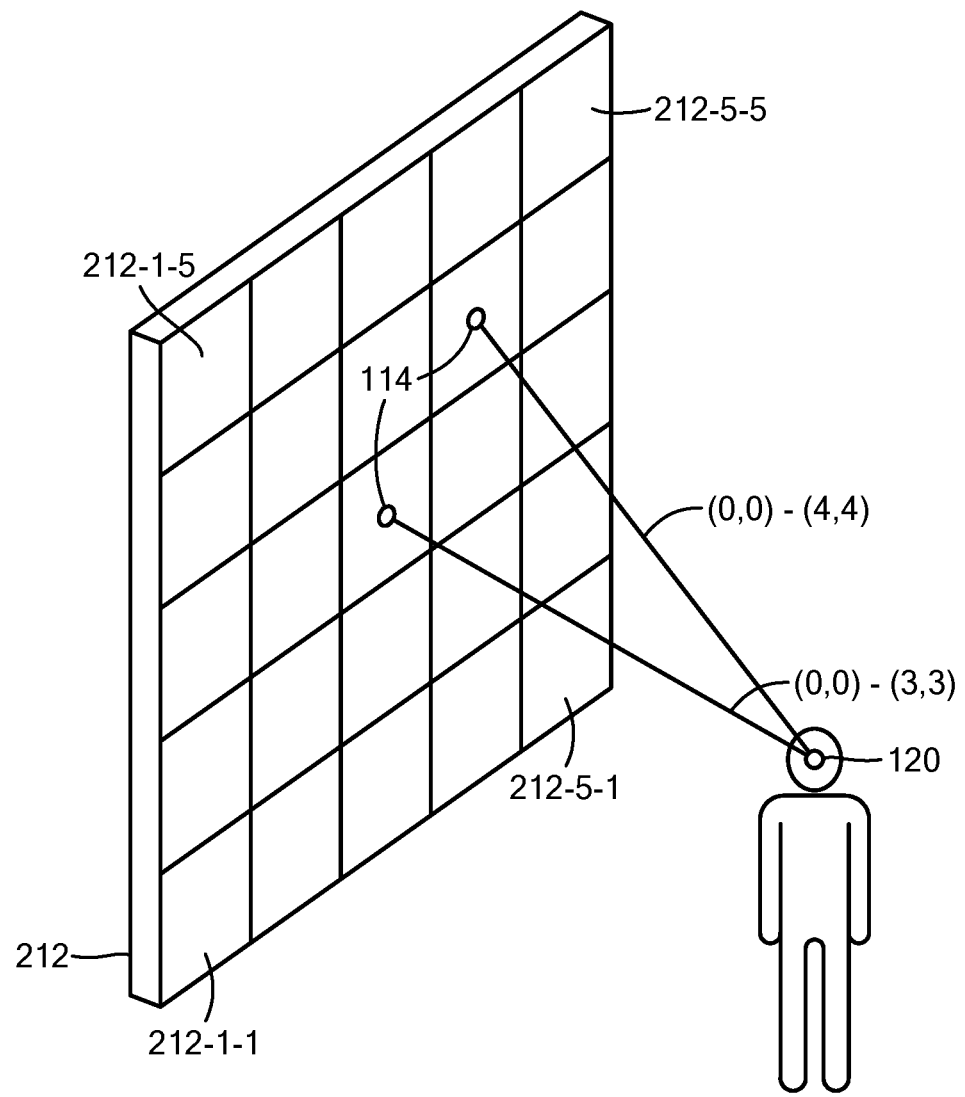
FIG. 2 is a perspective view of a two dimensional array of visual markers in the configuration of FIG. 1.

FIG. 2 is a perspective view of a two dimensional array of visual markers 212-1-1 . . . 212-5-5 (212 generally) in the configuration of FIG. 1. In FIG. 2, the array 212 of visual markers 114 is a two dimensional arrangement of symbols, such that each symbol is visually distinguishable from at least an adjacent symbol. Any suitable symbol may be employed that allows the subject to generate an indication of the symbols within their field of view for defining an outer periphery of the FOV. The array 212 of visual markers 114 may therefore include opposed right and left arrays of visual markers, each of the opposed right and left visual markers defining left and right FOV portions. The two dimensional arrangement defines a grid location for each position in the array 212. The two dimensional array of visual markers 212 also defines a mapping 150 as in FIG. 1, however allows variance in the vertical direction as well as the horizontal. The peripheral vision is most capable, or broad, in a direction level with the eyes. As the periphery is adjusted upwards or down, the peripheral vision generally becomes less accurate and object need to be more aligned towards the front facing view. In other words, as the visual marker is viewed at a higher or lower angle, the visual marker needs to be in a more forward position.

Figure 3:
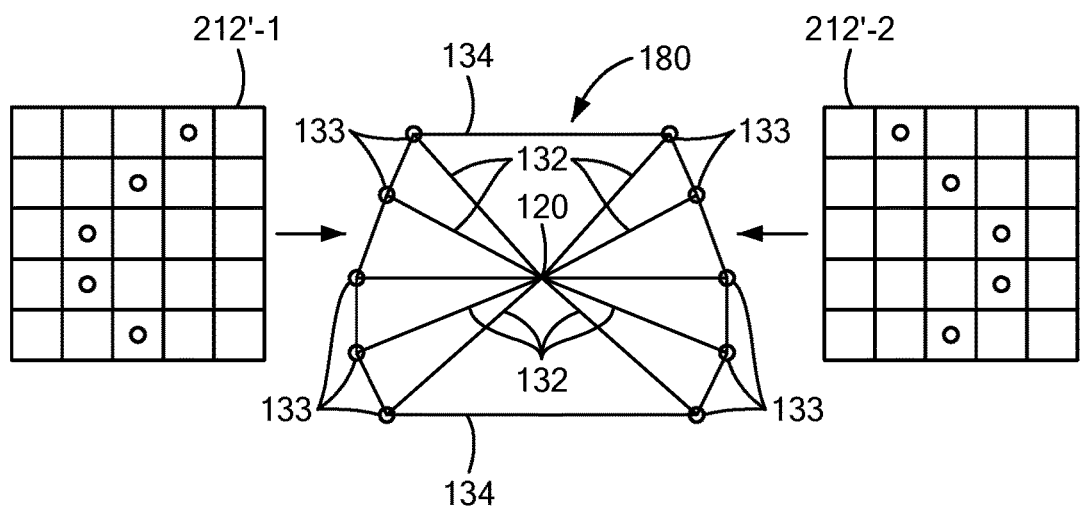
FIG. 3 shows the polyhedron resulting from the mapping of the visual markers of FIG. 2.

FIG. 3 shows the polyhedron resulting from the mapping of the visual markers of FIG. 2. Referring to FIGS. 1-3, in operation, a subject 110 with their head (viewpoint) at the origin 120 defined by the chinrest 142 reports the discernable symbols in the visual marker arrays 212. Any suitable symbols may be employed, such as the polygon shapes of the single dimensioned marker arrays 112, numerical symbols, colored lights, or any other visually discernable symbol reported by a subject for input. Based on the mapped array position, a distance and direction to the marker 114 is defined. In FIG. 3, front elevation views of the marker arrays 212'-1 and 212'-2 are shown, including marked grid positions "o" based on the inputs resulting form visually ascertainable markers 114. As alluded above, the grid pattern appears roughly as a pair of opposed parentheses, as the visual field on an even plane with the line of sight gives the widest visual angle.

The polyhedron 180 is defined by edges 132 based on the origin 120 and vertices 133 of each of the marked grid positions from the reported inputs of visible markers 114. If top (above field of view) and bottom (floor/below field of view) marker arrays 212 are not used, projections 134 based on the highest/lowest vertices or other boundary are used to bound the polyhedron 180.

Figure 4:
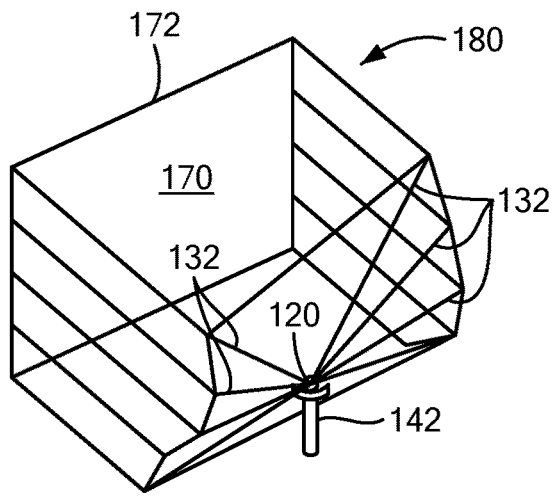
FIG. 4 shows a perspective view of the edges and vertices defining a polyhedron as in FIG. 3.

FIG. 4 shows a perspective view of the edges 132 and vertices defining the polyhedron 180 as in FIG. 3. Referring to FIGS. 1-4, edges 132 emanating from the vertex defined by the origin 120 extend to the vertices 133 defined by the marker arrays 112, typically in a plane if the marker array 212 is planar (it need not be). This defines the edges 132 of the polyhedron 180 based on the mapped positions 114, such that each of the edges 132 is defined by vertices at the origin of the field of vision and a respective position 114. The FOV origin 120 is based on the chin rest 142 adapted for engaging a subject of an FOV assessment, wherein the origin 120 approximates visual stimuli received by either a right or left eye. The origin could be calibrated to reflect an offset to an eye of the subject, such as several inches up and right or left an inch or two, but such fine tuning is unlikely to affect the computed volume substantially.

Figure 5:
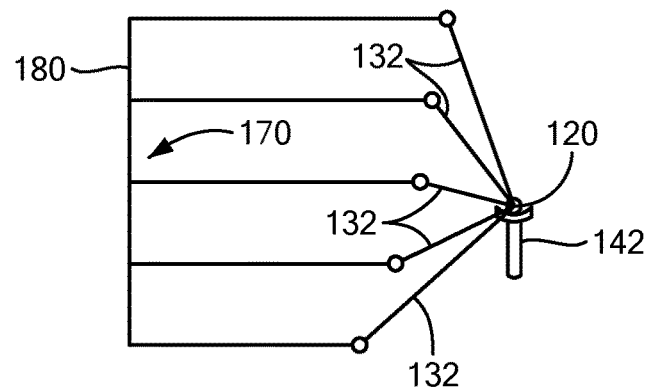
FIG. 5 shows an elevation of the resulting polyhedron.

A forward field of view may be bounded by a predetermined distance, and should be a constant distance from the chin rest to assure control between iterations of marker positions. This includes closing the polyhedron by defining a polygon 170 based on a plane at a predetermined distance and direction from the origin 120 of the field of vision. In other words, in order to provide a consistent set of quantifications from successive subject iterations, polyhedron boundaries other than the edges 132 between the origin 120 and the markers 114 should remain constant. The distance from the origin 120 to the polygon 170 may be tuned to give an "inertia" to the FOV volume calculation FIG. 5 shows an elevation of the resulting polyhedron 180. Referring to FIGS. 3-5, the chin rest 142 defines the origin 120 from which the edges 132 emanate. The set of vertices 114 defined by the marker array 212 likely take an annular form, as the FOV angle is widest when level with the origin 120, and tapers at the upper and lower ranges.

A volume calculation of the polyhedron 180 gives an accurate indication of the FOV of the subject, based on the observed and reported markers. As the FOV narrows or decreases, the reported markers 114 are at positions more forward in the array 212, and therefore have an effect of reducing the computed volume of the polyhedron 180. This measurement gives an accurate rendering of at least peripheral vision of a subject, and is particularly useful as a baseline. A successive series of reported markers, taken from a similar origin and forward boundary definition, can indicate if the FOV is decreasing based on whether the computed volume is decreasing.

The examples above show marker arrays in four orientations: right, left, above and below. Additional marker positioning may be employed, and they need not lie coplanar with other markers, as long as an accurate position from the origin may be defined by the mapping. The defined polyhedron 172 may be based on a variable number of edges, generally defined by vertices at the origin and the marker locations. Additional markers/edges result in increased accuracy of the FOV calculation based on a more specifically defined polyhedron. Since the FOV tends to narrow above and below a plane defining the forward line of sight, additional marker 114 positions in the upper and lower regions of the FOV will tend to indicate declining peripheral vision in these regions.

Once edges 132 based on marker 114 positions are defined, the polyhedron 180 is bounded to define a finite volume. Bounding generally occurs in the forward FOV, at a distance from the origin 120, and along any regions where the marker positions are sparse. The volume is calculated based on the bounded polyhedron, and may be performed by any suitable mechanism. For example, certain applications perform 3-dimensional modeling for receiving a polyhedron definition, bounding it using a wrapping or perimeter function, and computing a volume of the wrapped volume. MATLAB® is one such application.

Figure 6:
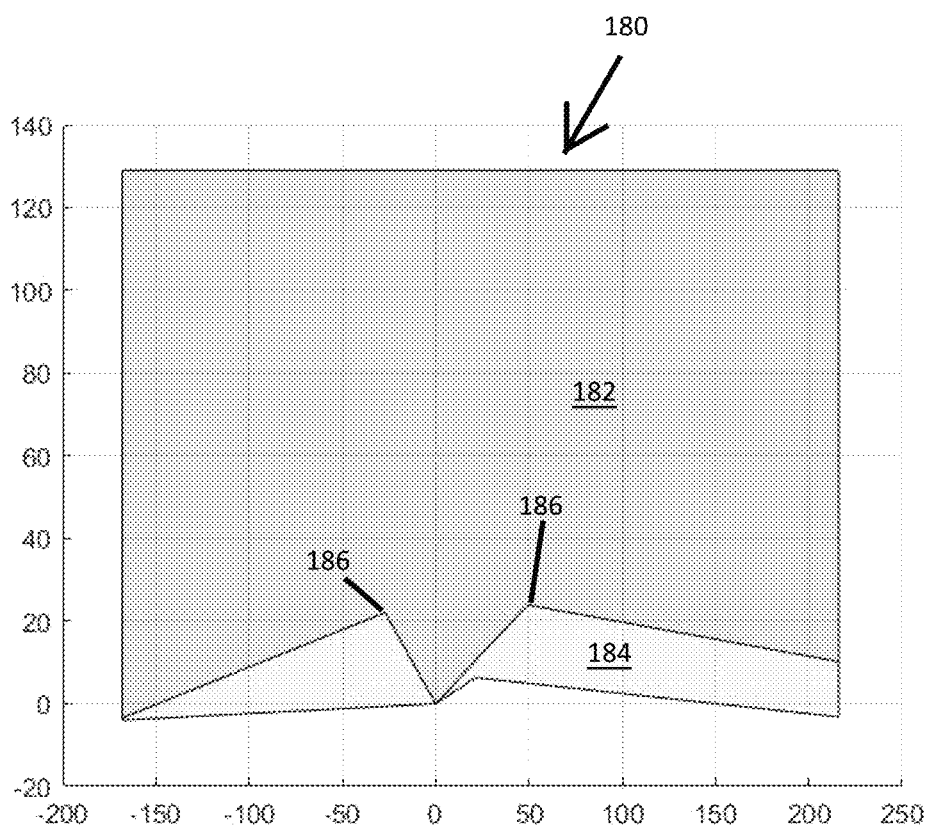
FIG. 6 shows a top (plan) view of the resulting polygon illustrating a visual range angle of the FOV.

FIG. 6 shows a top (plan) view of the resulting polygon illustrating a visual range angle of the FOV. Referring to FIGS. 3-6, the two dimensional rendering of FIG. 6 results from collapsing the polyhedron 180 in a vertical direction. FIG. 6 depicts a use case with FOV comparisons when using protective headgear and determining which has the least effect on the FOV. The broadest angle edge, meaning the edge most rear facing, defines the FOV following the collapse of the polyhedron 180. Two areas are depicted based on different masks employed by a subject. Since the effect of collapsing results in a single rearmost edge, and since the side and forward boundaries are constant, a variance in the FOV is shown by lines defined by vertices 186. An angle of the edge 132 drawn to the vertices (typically from center) can also be employed as a FOV parameter. Peripheral vision is usually about 90 degrees left and right, varying slightly either forward or back, meaning optimal peripheral vision may extend rearward by a few degrees.

In FIG. 6, a bottom array 212 of visual markers 114 was employed to assist in identifying impairment resulting from a nosepiece. Floor markers are therefore used to define edges 132. A first region 182 shows a region defining a FOV with a first facemask, such that the FOV was affected by the facemask. A second region 184 shows a different region illustrating an increase in FOV using the second facemask, Intermediate vertices 186 define a nosepiece of the facemask that obscures some of the FOV, further illustrating that any set of vertices may be employed for defining the polyhedron 180; they need not be aligned with a plane of the marker array 212.

Figure 7:
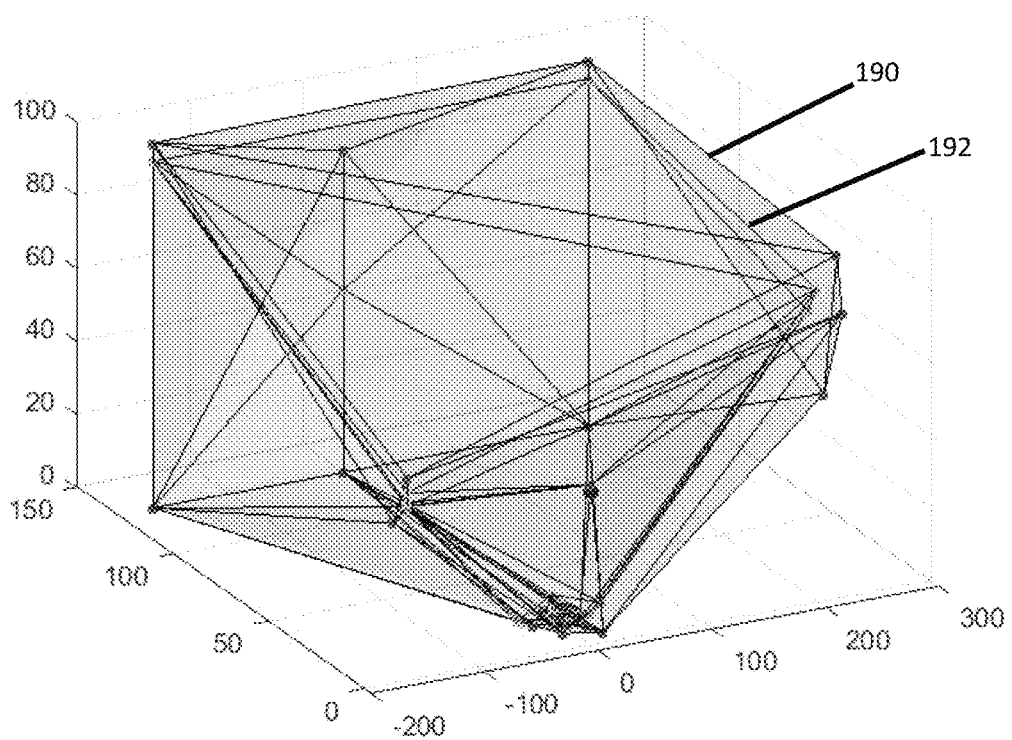
FIG. 7 shows a plurality of polyhedrons illustrating a delta from a baseline volume.

FIG. 7 shows a plurality of polyhedrons illustrating a delta from a baseline volume. In FIG. 7, a first polygon and a second polygon illustrate differences in volume from different sets of marker inputs. A first polyhedron 190 and second polyhedron 192 are shown shaded, to illustrate the difference in volume defined by each.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A vision field assessment device, comprising:
an array of visual markers approximating an outer range of a field of view, each visual marker having a position in the array;
the array referenced by a mapping from a field of view (FOV) origin to each visual marker in the array;
the mapping having a plurality of elements corresponding to the visual markers, each element in the plurality of elements storing a position from the FOV origin to the corresponding visual marker;
each position defining a vertex of a polyhedron and an edge from the origin, a volume of the polyhedron quantifying the field of view.

2. The device of claim 1 wherein the edge defines an angle of the FOV, the angle indicative of a radial spectrum of the FOV.

3. The device of claim 1 wherein the FOV origin is based on a chin rest adapted for engaging a subject of an FOV assessment, wherein the origin approximates visual stimuli received by either a right or left eye.

4. The device of claim 1 wherein the array of visual markers is defined by a two dimensional arrangement of symbols, each symbol visually distinguishable from at least an adjacent symbol, the two dimensional arrangement defining a grid location for each position in the array.

5. The device of claim 1 wherein the array of visual markers further comprises opposed right and left arrays of visual markers, each of the opposed right and left visual markers defining left and right FOV portions.

6. The device of claim 5 further comprising at least one of upper and lower arrays of visual markers, the upper array of visual markers disposed vertically above and between the right and left arrays of visual markers and the lower array of visual markers disposed vertically below and between the right and left arrays of vertical markers.

7. The device of claim 1 further comprising a defined side of the polyhedron, the defined side resulting in bounded volume of the polyhedron.

8. A method of quantifying a field of vision, comprising:
receiving a set of indications of a visual marker, each visual marker having a position in an array of visual markers;
mapping each of the indications to a position, the position defining a location relative to an origin of a field of vision;
defining a polyhedron, the polyhedron having edges defined by each of the positions and the origin of the field of vision; and
computing a volume of the defined polyhedron.

9. The method of claim 8 further comprising closing the polyhedron by defining a polygon based on a plane at a predetermined distance and direction from the origin of the field of vision.

10. The method of claim 8 further comprising defining the edges of the polyhedron based on the mapped positions, each of the edges defined by vertices at the origin of the field of vision and a respective position.

11. The method of claim 8 further comprising disposing the array of visual markers for approximating an outer range of a field of view, and
generating the mapping from a field of view (FOV) origin to the position of each visual marker in the array.

12. The method of claim 11 wherein the field of view is defined by a chin rest engaged by the subject.

13. The method of claim 8 wherein the array of visual markers is a two dimensional arrangement of symbols, each symbol visually distinguishable from at least an adjacent symbol, the two dimensional arrangement defining a grid location for each position in the array.

14. The method of claim 8 further comprising receiving a series of positions based on visual markers, each position in the series of positions defining a location relative to an origin of a field of vision.

15. A system for defining and assessing a Field of View (FOV), comprising:
an array of visual markers defining an outer range of the FOV, each visual marker having a position in the array;

a FOV origin defining a reference perspective of a visually perceptible area;

a mapping from the FOV origin to each visual marker in the array, the mapping having a plurality of elements corresponding to the visual markers, each element in the plurality of elements storing a position of the respective visual marker relative to the FOV origin;

a polyhedron bounded by vertices defined by a vector based on each of the elements in the mapping, and a volume based on the polyhedron, the volume of the polyhedron indicative of a relative increase or decrease in the FOV.

* * * * *